(12) United States Patent
Rogozinski

(10) Patent No.: US 6,336,927 B2
(45) Date of Patent: *Jan. 8, 2002

(54) APPARATUS, METHOD AND SYSTEM FOR THE TREATMENT OF SPINAL CONDITIONS AND FIXATION OF PELVIS AND LONG BONES

(76) Inventor: Chaim Rogozinski, 3223 Front Rd., Jacksonville, FL (US) 32217

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/222,727

(22) Filed: Dec. 29, 1998

Related U.S. Application Data

(60) Division of application No. 08/898,862, filed on Jul. 23, 1997, now Pat. No. 5,904,682, which is a division of application No. 08/692,821, filed on Jul. 29, 1996, now Pat. No. 5,716,357, which is a continuation of application No. 08/448,566, filed on Jun. 7, 1995, now abandoned, and a continuation of application No. PCT/US94/11463, filed on Oct. 7, 1994.

(51) Int. Cl.[7] ............................................. A61B 17/70
(52) U.S. Cl. .............................. 606/61; 606/72; 606/69
(58) Field of Search ............................. 606/60, 61, 69, 606/70, 71, 72, 73, 75, 104, 105; 623/17.11

(56) References Cited

U.S. PATENT DOCUMENTS

| | | | | |
|---|---|---|---|---|
| 2,780,223 A | * | 2/1957 | Haggland | 606/69 |
| 3,693,616 A | * | 9/1972 | Roaf et al. | 606/61 |
| 4,085,744 A | * | 4/1978 | Lewis et al. | 128/69 |
| 4,959,065 A | * | 9/1990 | Arnett et al. | 606/69 |
| 5,092,893 A | * | 3/1992 | Smith | 623/17 |
| 5,415,661 A | * | 5/1995 | Holmes | 606/69 |
| 5,716,357 A | * | 2/1998 | Rogozinski | 606/61 |
| 5,718,704 A | * | 2/1998 | Medoff | 606/69 |

* cited by examiner

Primary Examiner—David O. Reip
(74) Attorney, Agent, or Firm—Thomas C. Saitta

(57) ABSTRACT

An apparatus, method and system for treating spinal conditions by moving or spatially fixing at least one vertebra relative to another vertebra. The invention includes a link member the ends of which are configured to be secured to adjacent vertebrae and which are offset from a central portion of the link member. The link members can be in the form of a C-shaped or V-shaped rod or plate to form the offset. The offset provides increased bone volume that can be used for grafts or fusion. Attachment structure in the form of bone screws, bolts, or hook members are provided to secure the link members to respective vertebrae or other bones. A plurality of link members can be connected in chain-like fashion to connect multiple points on a plurality of vertebrae or other bones even though those points are nonlinear. In another aspect of the invention, a multi-directional attachment member is provided and may be used with the link members to form a spinal implant or external bone fixation system.

7 Claims, 8 Drawing Sheets

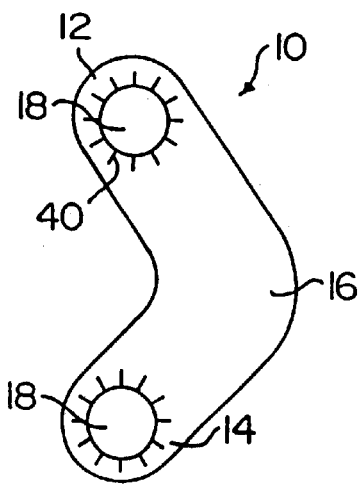
FIG. IA
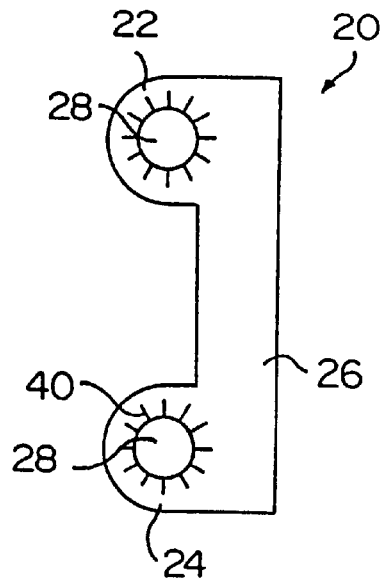
FIG. IB
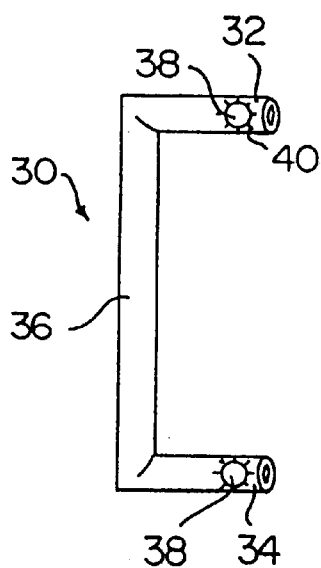
FIG. IC

FIG. 7
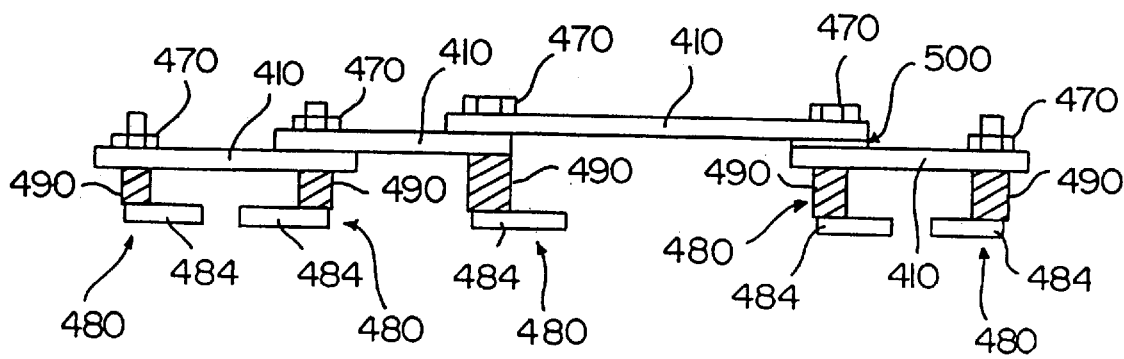
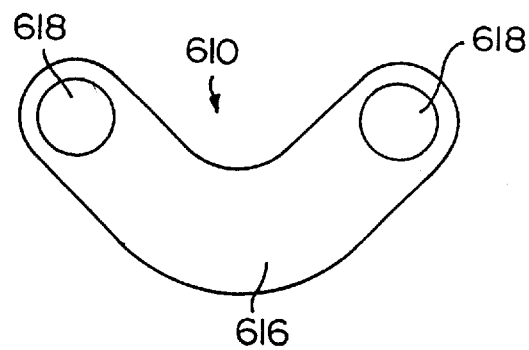
FIG. 8A
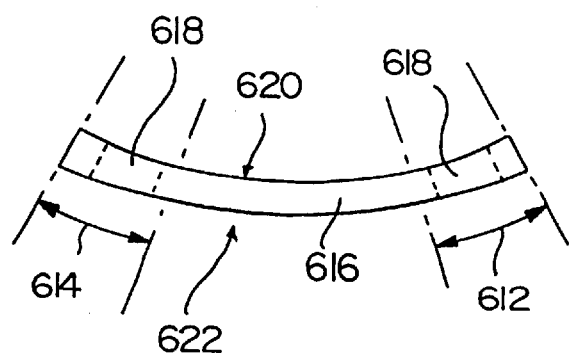
FIG. 8B

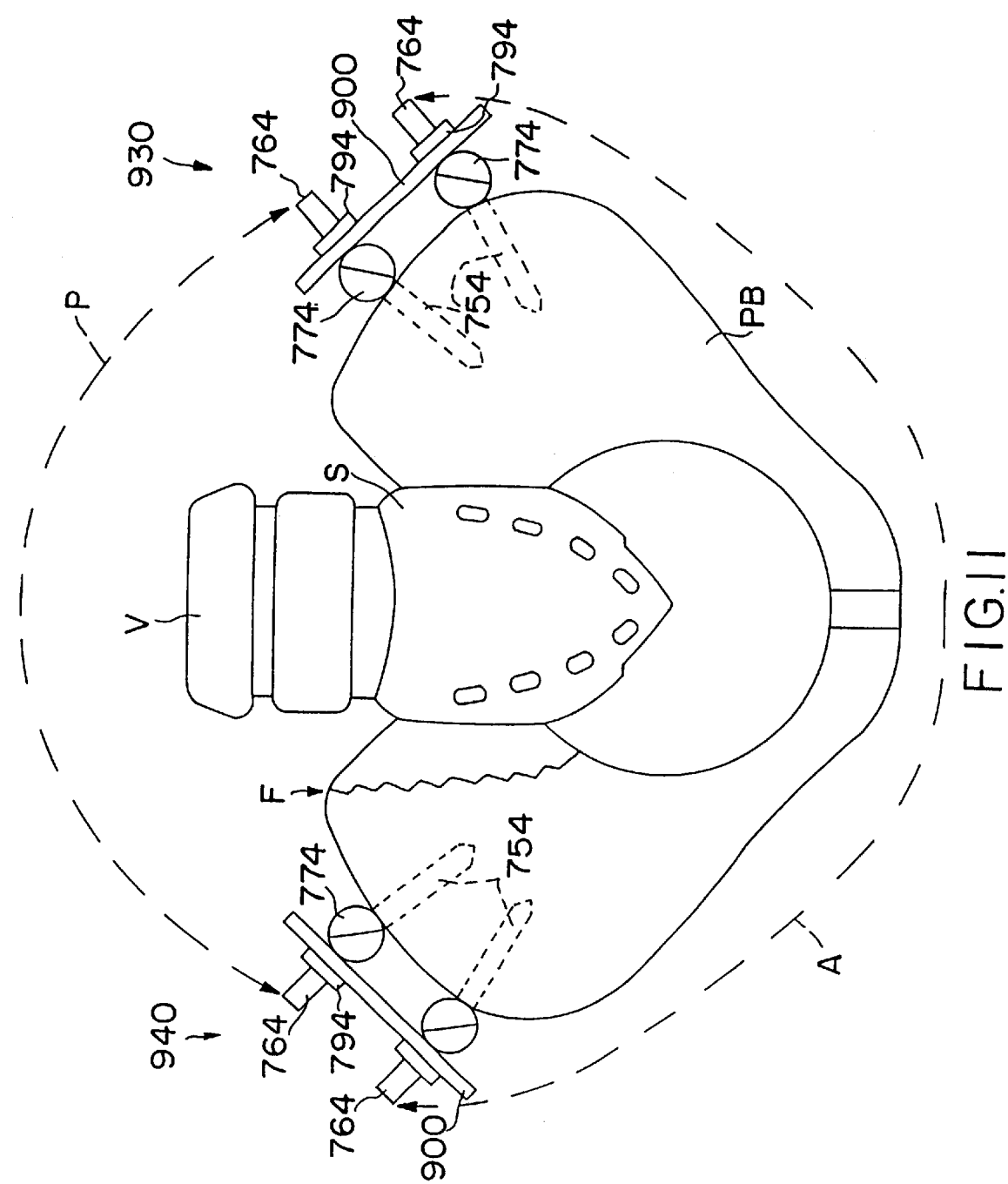

APPARATUS, METHOD AND SYSTEM FOR THE TREATMENT OF SPINAL CONDITIONS AND FIXATION OF PELVIS AND LONG BONES

This is a division of application Ser. No. 08/898,862 filed Jul. 23, 1997, now U.S. Pat. No. 5,904,682, which in turn is a division of Ser. No. 08/692,821 filed Jul. 29, 1996, now U.S. Pat. No. 5,716,357, which in turn is a continuation of Ser. No. 08/448,566 filed Jun. 7, 1995, now abandoned, and of PCT/US94/11463 filed Oct. 7, 1994.

BACKGROUND OF THE INVENTION

1. Field of the Invention

The present invention relates generally to apparatus and methods for treating and correcting spinal abnormalities or conditions, stabilizing the position of the spine and vertebrae thereof and fixing or moving the position of bones other than those in the spine. More specifically, the present invention provides an apparatus and system which includes a plurality of links usable together under various circumstances to treat, e.g., different spinal curvature conditions or bone fractures.

2. Description of the Relevant Art

The prior art includes many different apparatus and methods for treating spinal conditions. Known apparatus utilize elongate plate members having several aligned openings or an elongated slot therein for receiving screws or bolts that are affixed to vertebrae. The plate is secured to the screws or bolts and exerts force on the selected vertebra or vertebrae to move same into a desired position or to maintain same in a desired position. The plate also overlies the majority of the lateral bone surface of the vertebrae.

In using such known plate systems, a problem arises when the points on the vertebrae defined by the screws or bolts are not collinear, i.e., they do not lie in a straight line. This creates a problem for the physician because the openings in the plate are collinear and, therefore, the screws do not line up with the plate openings. The physician has several options to compensate for such nonalignment, all of which present additional problems themselves.

The plate can be contoured in the frontal plane to attempt to line the screws up with the plate openings. Due to the thickness and high strength of the plate, this is essentially impossible to do intraoperatively. Another option is to bend the screws or bolts so that they fit in the slots or openings in the plate. This creates an immediate high stress region in the screw or bolt which can cause failure of the same upon cyclical loading or, even worse, can lead to a fracture of the pedicle of the vertebra.

A third option is to place the screws or bolts in a less than optimum position or trajectory in the pedicle of the vertebra so that they line up with the plate openings. This too can lead to pedicle fractures or cut-out, as well as nerve root injury.

Other known apparatus for treating spinal deformities are disclosed in U.S. Pat. Nos. 5,102,412 and 5,181,917. These apparatus include elongate rod members which have vertebra engaging means secured thereto in an adjustable fashion. The apparatus can be used with bone bolts or screws, or laminar or pedicle hooks. However, the rods are essentially straight which makes utilizing nonlinear points of connection on adjacent vertebrae difficult without the use of specially formed components. In addition, spinal apparatus and systems such as those disclosed in the aforementioned patents include a large number of moving parts and therefore are inherently susceptible to malfunction.

Accordingly, there is a need in the art for a method and apparatus for treating spinal conditions which avoids the problems of the prior art, permits attachment to nonlinear points on adjacent vertebrae, and provides increased bone volume for grafts and fusion.

The prior art includes various apparatus for the treatment of non-spinal conditions, e.g., in long bones and the pelvis. Such conditions include fractures, joint fusions, osteotomies, etc. The prior art apparatus for treating the aforesaid non-spinal conditions do not permit attachment of the bone fixation device to non-linear attachment points on the bone or bones being treated. Accordingly, there is a need in the art for an improved apparatus and method for the treatment of non-spinal conditions.

SUMMARY OF THE INVENTION

The present invention provides an apparatus and method for treating spinal conditions by moving a vertebra to a desired position with respect to additional vertebrae or maintaining the vertebra in the desired position.

The apparatus of the present invention includes a plurality of link members that can be secured to adjacent vertebrae in chain-like fashion utilizing pedicle bolts or screws that are not collinear with each other. The link members can be used to subdivide multiple nonlinear pedicle fixation points into units of two adjacent points which two points can be interconnected with a single link member.

The present invention thus facilitates multiple point fixation using two points at a time to overcome the problem in the prior art of nonalignment between plate openings and pedicle screws. The links form a chain and once they are secured to the pedicle screw or bolt with a locking nut, the result is a rigid construct securely affixed to the vertebrae.

The link members are in the form of plates or rods with opposite end portions and a central portion. The opposite end portions each have an aperture therein configured to receive attachment means affixed to the pedicle of adjacent vertebrae. The central portion of each link member is preferably offset from the end portions so that when the link member is attached to adjacent vertebrae portions of the latter are substantially uncovered by the link central portion. However, the present invention also includes links in which the central portion is not offset.

This offset provides increased vertebrae bone volume as compared with prior art apparatus which overlie the vertebra surface, which increased bone volume can be used for bone grafts and fusion. In addition, the present invention permits visualization of bony maturation using plain X-rays since the links do not overlie the graft area.

The links of the present invention can be used with and secured to pedicle screws, bolts, or pedicle or laminar hooks. A combination of hooks and screws or bolts can be used as well depending on the particular application of the invention. For example, a laminar hook can be used on a lamina that is being fused to avoid damaging its associated facet (joint) such as would be caused by a screw or bolt.

The surface of the link member of the present invention is preferably provided adjacent the apertures in the end portions thereof with radial cuts or other interdigitating structure for facilitating and enhancing the locking engagement of the links with a pedicle bolt, screw, hook, or other link(s) at a desired relative position. The bolt or hook has a threaded extension portion that cooperates with a locking nut, and a wedge-shaped washer if needed, to secure an end of the link member to a vertebra.

The wedge-shaped washer compensates for a lack of parallelism in the axial plane between adjacent bolts or screws.

An additional aspect of the present invention is that link members can be used to secure contralateral chains (formed as described above) to each other at their ends, and/or points intermediate their ends, to form a quadrilateral or ladder-shaped construct having increased torsional stability.

A further aspect of the present invention provides a multi-directional attachment assembly which includes a screw portion or member threaded for engagement with a bore formed in a bone, and a bolt portion or member threaded to receive a plate, rod, etc., and a complimentary threaded locking nut. The bolt portion is adjustable with respect to the screw portion and can be positioned in a location that is optimal with regard to receiving and supporting the aforementioned plate, rod, etc. The bolt portion may be angularly positioned relative the screw portion so that the former engages the plate or rod in a desired manner, for example, a perpendicular fashion. The bolt and screw portions preferably include mating hemispherical portions which are joined on a plane that is oblique to the longitudinal axis of both the screw and bolt portions. The multi-directional attachment device may be used with spinal fixation systems to facilitate optimal placement of the screw portion within the vertebra while permitting adjustment of the bolt portion relative thereto for optimal engagement with the plate and/or rod. In addition, the above-described link structures and multi-directional attachment members may be used in the treatment of non-spinal conditions including fractures, joint fusions, osteotomies, etc.

BRIEF DESCRIPTION OF THE DRAWINGS

Additional features of the present invention will be apparent to those skilled in the art from the following detailed description when considered in conjunction with the accompanying drawings, wherein:

FIG. 1A is a front elevational view of a link member according to a first embodiment of the present invention;

FIG. 1B is a front elevational view of a link member according to another embodiment of the present invention;

FIG. 1C is a front elevational view of a link member according to another embodiment of the present invention;

FIG. 7 is a side elevational view showing a plurality of link members according to the present invention secured together by pedicle or laminar hook members and looking nuts;

FIGS. 8A and 8B are, respectively, front and side elevational views of a curved link member according to another embodiment of the present invention;

FIG. 11 is a front elevational view of the link member and multi-directional attachment device of the present invention used as a pelvic bone fixation apparatus.

DETAILED DESCRIPTION OF THE PREFERRED EMBODIMENTS

Figure 2:
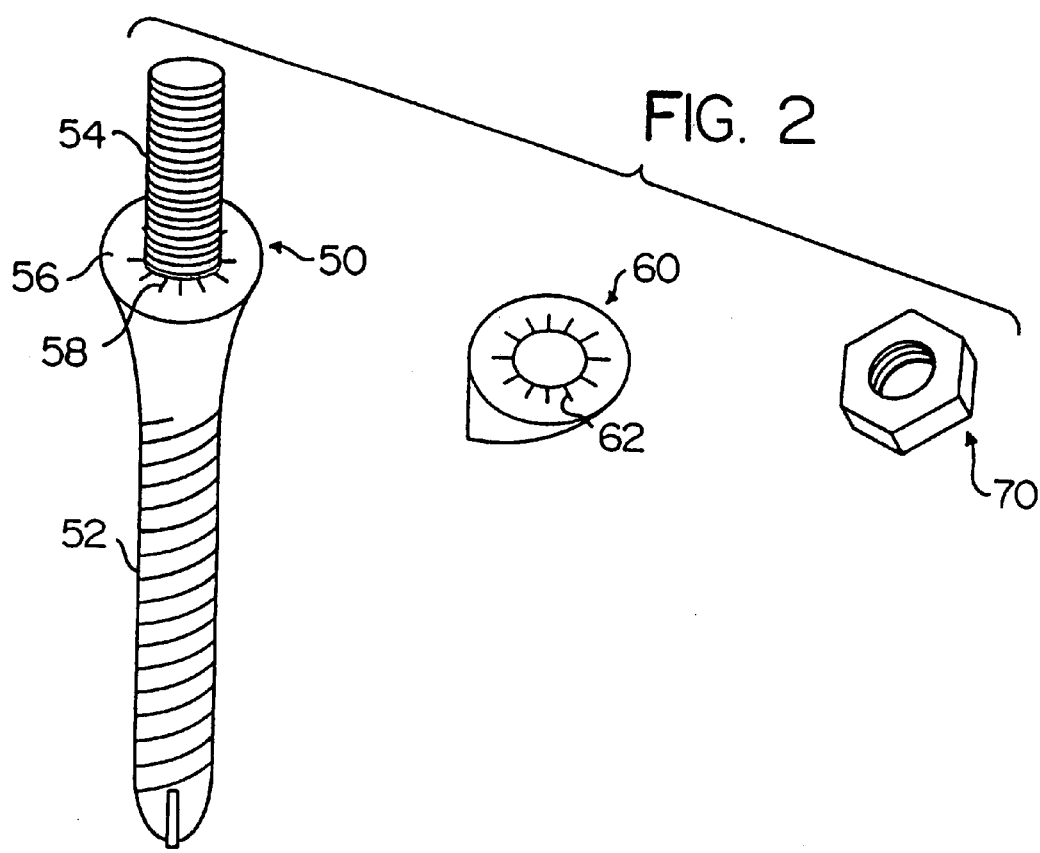
FIG. 2 is an exploded view of a pedicle or bone bolt, a washer, and a locking nut according to the present invention.

With reference to FIG. 1A, a link member according to a first embodiment of the present invention is indicated generally by the reference numeral 10 and includes first and second end portions 12, 14 and a central portion 16. The end portions 12, 14 each have an aperture 18 therein which apertures are configured to receive a threaded bone bolt or screw, or a laminar or pedicle hook, to secure the link 10 to adjacent vertebrae as will be described below. The link 10 is preferably integrally formed so as to comprise a one-piece structure. The link in the embodiment of FIG. 1A is in the form of a plate and is substantially V-shaped with the central portion 16 comprising the apex of the V shape.

FIG. 1B shows another embodiment of the link according to the present invention indicated generally at 20. Link 20 includes first and second end portions 22, 24 and a straight central portion 26. The end portions 22, 24 each have an aperture 28 similar to the apertures 18 in link 10. Link 20 also is in the form of a plate which plate is substantially C-shaped. The C-shape of link 20, like the V-shape of the link 10 shown in FIG. 1A, provides the link with end portions that are offset from the central portion for reasons discussed below.

FIG. 1C shows another embodiment of a link according to the present invention which link is indicated at 30 and includes end portions 32, 34 and central portion 36. The link 30 is in the form of a C-shaped rod member having a cylindrical cross-section. It will be appreciated that the cross-sectional shape of link 30 can be noncylindrical and that link 30 can be a rod member that is V-shaped similar to link 10 in FIG. 1A. The ends 32, 34 have an aperture 38 disposed therein for receiving pedicle bolts, screws or hooks as in the aforementioned embodiments for reasons as will be described below.

The present invention also includes link members in which the end portions and the central portion are aligned, i.e., not offset, which links can be connected in chain-like fashion to follow a nonlinear path. For example, see links 240 in FIG. 5. In an alternative embodiment, the non-offset links can be in the form of a rod with a cylindrical or noncylindrical cross-section or, the links can be in the form of other suitably shaped structure.

However, the links preferably have the respective end portions offset from the central portion as in links 10, 20 and 30. This offset is formed such that a line passing through the midpoint of the apertures formed in the end portions of links 10, 20 and 30 does not overlie the central portion of the link. See the dashed line in FIGS. 1A or 1C. While the illustrated links are V-shaped and C-shaped, those of ordinary skill in the art will recognize that other shapes are possible as long as the central portion of the link is at least partially offset from the end portions thereof.

Figure 5:
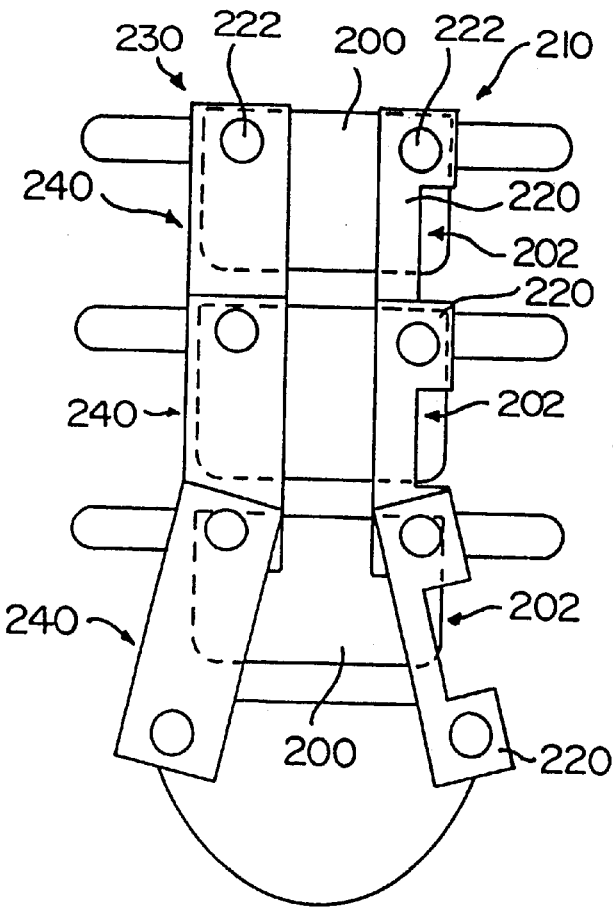
FIG. 5 is a front elevational view showing a plurality of the link members depicted in FIG. 1B, comparing them to link members in which the central portion is not offset.

FIG. 5 shows two rigid constructs 210, 230 formed of a plurality of links 220, 240, respectively. Constructs 210 and 230 are secured to the plurality of vertebrae 200 by means indicated schematically at 222 and 232, respectively. The securing means can be in the form of bone screws, bolts or hook members as will be explained in detail below. Links 220 of construct 210 have an offset central portion which leaves the lateral margin 202 on one side of the vertebrae 200 (to which the links are secured) substantially uncovered. However, links 240 of construct 230 do not have such an offset and thus the lateral margins on that side of vertebrae 200 are covered by the links 230.

The offset links 220 provide additional bone volume or surface that can be used for grafts, fusion, etc. In addition, because the bone surface is uncovered, a physician can view the bony maturation of the vertebrae being treated with plain X-rays. This is very difficult in prior art systems in which the elongated plates or rods overlie the graft area.

FIG. 2 shows a pedicle or bone bolt 50 used with the link members of the present invention to secure the same to vertebrae. While FIG. 2 shows a bone bolt, it will be recognized that a bone screw, e.g. a threaded member having a head which forces the link member against the bone surface, can also be used. The use of bone bolts and screws to secure spinal curvature apparatus to vertebrae by placing the same in bores formed in the vertebrae is generally known and will not be described in detail. As will be discussed below, it is also possible to use laminar or pedicle hook members in place of or in combination with the bone bolts or screws. The engagement of such attachment members with vertebrae is discussed in aforementioned U.S. Pat. Nos. 5,102,412 and 5,181,917 granted to the present applicant, the subject matter of which patents is incorporated herein by reference.

The bone bolt 50 shown in FIG. 2 includes a helical portion 52, i.e., a portion having a helical thread or cutting surface for locking the bolt within a bore formed in a vertebra (not shown). An upper portion 54 of bolt 50 is threaded to receive a locking nut such as that shown at reference numeral 70 in FIG. 2. A shoulder portion 56 is disposed between the aforementioned portions 52 and 54.

After determining the proper position on the vertebrae, a bore is formed for each bolt as is known in the art and the bolt 50 is secured to a first vertebra (not shown) with shoulder 56 and threaded portion 54 extending therefrom. The aperture end of a link member (e.g., link members 10, 20 or 30) is positioned over the threaded portion 54 with the link member resting on shoulder 56. The shoulder 56 is provided with means for enhancing the engagement between the link member and the bone screw which means can be in the form of radial cuts 58, or any other suitable means such as roughened surfaces that aids in locking the link to the screw. With one end of the link member fastened to a first vertebra, the other end of the link member is positioned on a bolt 50 that is similarly secured to a second adjacent vertebra so as to move or lock one vertebra relative to the other vertebra.

A washer member 60 is shown which preferably is wedge-shaped and is configured to slide over the threaded portion 54 of bone bolt 50. The wedge shaped washer 60 can be used to secure a link member (not shown in FIG. 2) to a bolt, screw or hook member that is attached to a vertebra and forms an angle therewith. The washer 60 is placed on the shoulder 56 so that the link member forms substantially a right angle with the longitudinal axis of the bone bolt. Locking nut 70 then is threaded over portion 54 of bolt 50. The washer member 60 also preferably has radial cuts or other means for rotationally locking the link to the washer to provide overall torsional stability to the assembly.

Figure 4:
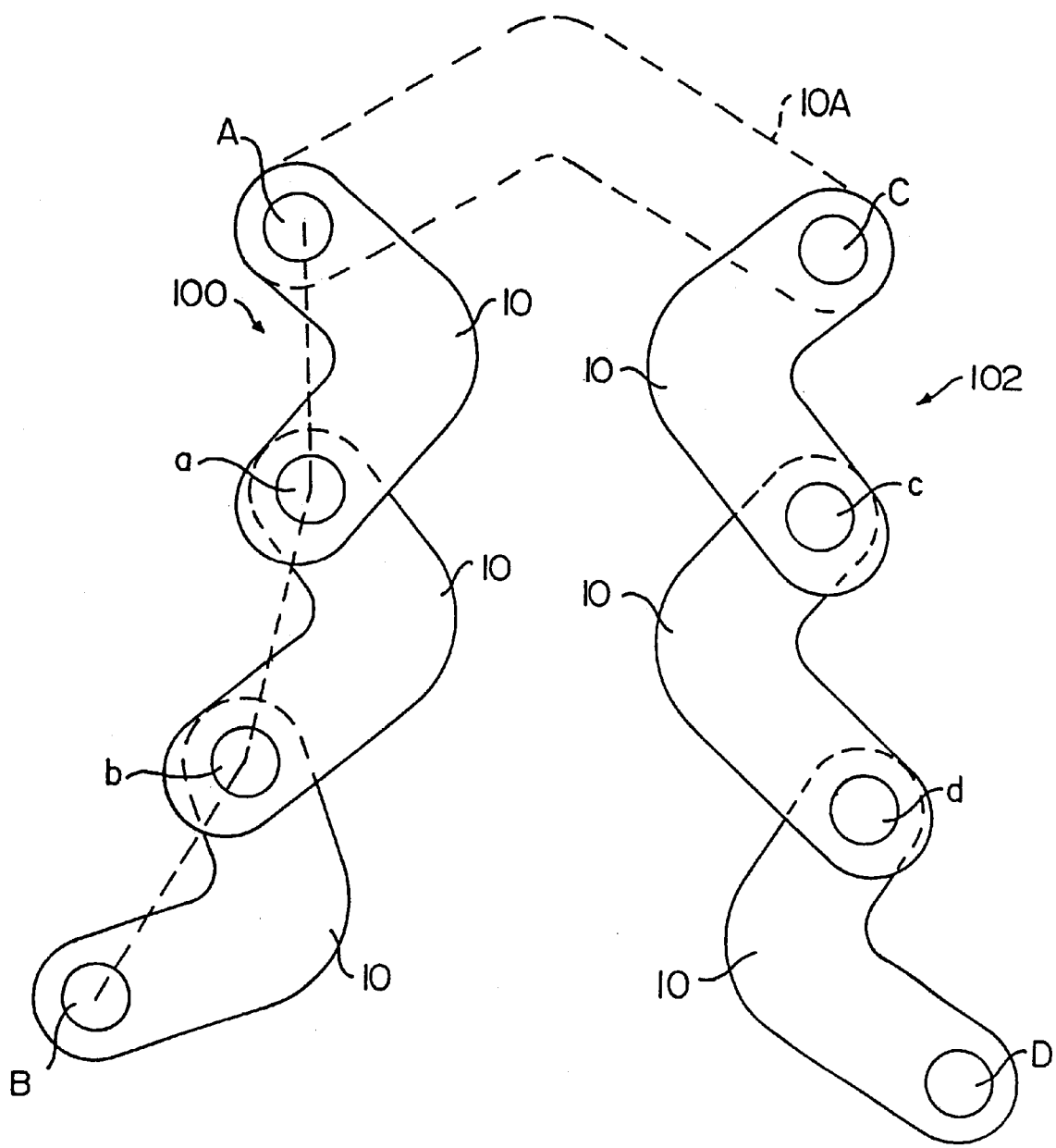
FIG. 4 is a front elevational view showing a plurality of the link members depicted in FIG. 1A placed together to form a chain-like construct.

FIG. 4 shows rigid constructs 100 and 102 formed of a plurality of link members 10 secured to each other in chain-like fashion. As seen therein, the links 10 are positioned with the end of one link overlying the end of an adjacent link. As also seen therein with respect to the construct 100 (on the left hand side of FIG. 4), a line passing through the midpoints of connection points A, a, b and B does not follow a linear path. The same is true with regard to the construct 102 and connection points C, c, d and D.

It is apparent that the aforementioned four connection points of either construct 100 or 102 are nonlinear and could not be connected using a conventional flat plate with a plurality of, e.g. four, linearly aligned openings. The same is true with regard to a prior art plate having an elongated linear slot or opening in which is positioned a plurality of bone bolts or other attachment structure. It will, of course, be recognized that the four connection points depicted in FIG. 4 are for exemplary purposes only and that it is possible to use more or less vertebrae attachment points. This aspect of the present invention permits a rigid construct to be formed using multiple vertebrae attachment points notwithstanding the fact those points do not lie in a straight line. This was not possible with prior art plates having linearly aligned multiple openings.

Also shown in FIG. 4 is a link member 10A, depicted in phantom, which serves as a cross-tie mechanism that secures the distal most connection points A and C of the constructs 100 and 102, respectively. While not shown in FIG. 4, a link member preferably is used on the opposite distal end points B and D. This results in a quadrilateral construct that stabilizes the chain-like construct both torsionally and in the frontal plane, as well as increases the strength required to pull the screws out of the vertebrae. Further, such cross-tie mechanisms can be used as well at points intermediate the distal most connection points of the chain-like constructs.

Figure 6:
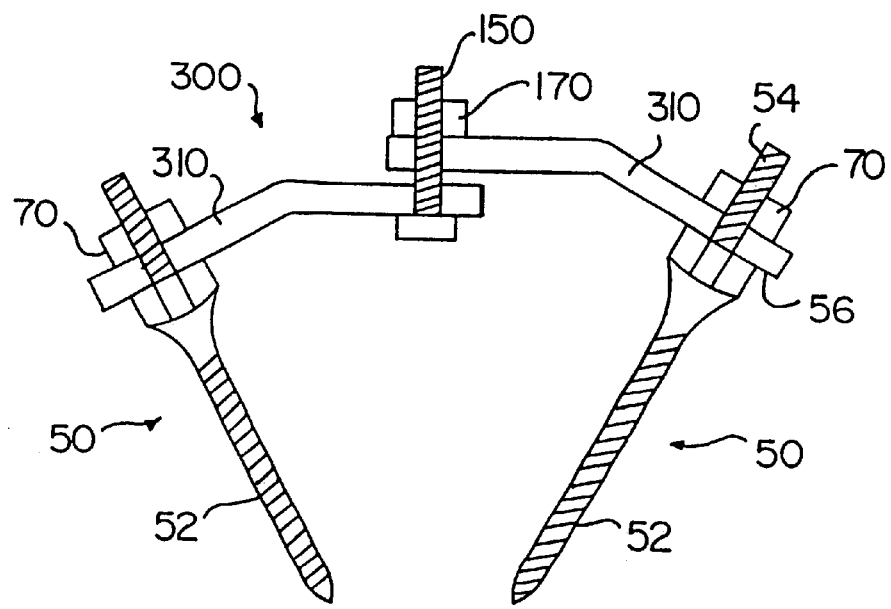
FIG. 6 is a side elevational view, partly in section, showing two bone bolts and a locking bolt securing together two link members in a delta configuration according to the present invention.

A further embodiment of the present invention is shown in FIG. 6 and includes a cross-tie mechanism 300 to provide a quadrilateral construct similar to that discussed above. The cross-tie mechanism 300 includes two links 310 that are produced according to the teachings of the present invention which links are secured to respective bolts 50 substantially as described above. That is, locking nuts 70 cooperate with threaded portions 54 of bolts 50 to attach the tatter to the links 310.

The ends of the links 310 opposite bone bolts 50 are secured to each other by a locking bolt 150 and nut 170. The ends of the links 310 are overlapped on the bolt 150 and the nut 170 is threaded over and secured to the bolt 150 to lock thee entire assembly. The cross-tie mechanism 300 provides a rigid quadrilateral construct which increases the torsional stability and pull-out strength. As seen in FIG. 6, bone bolts So are disposed in respective vertebrae (not shown) in a converging fashion which, when combined with a cross-tie mechanism, provide a configuration which increases the overall pull-out strength of the assembly. The cross-tie mechanism 300 also can be used at different locations along the length of the two constructs to form a ladder configuration.

Figure 3:
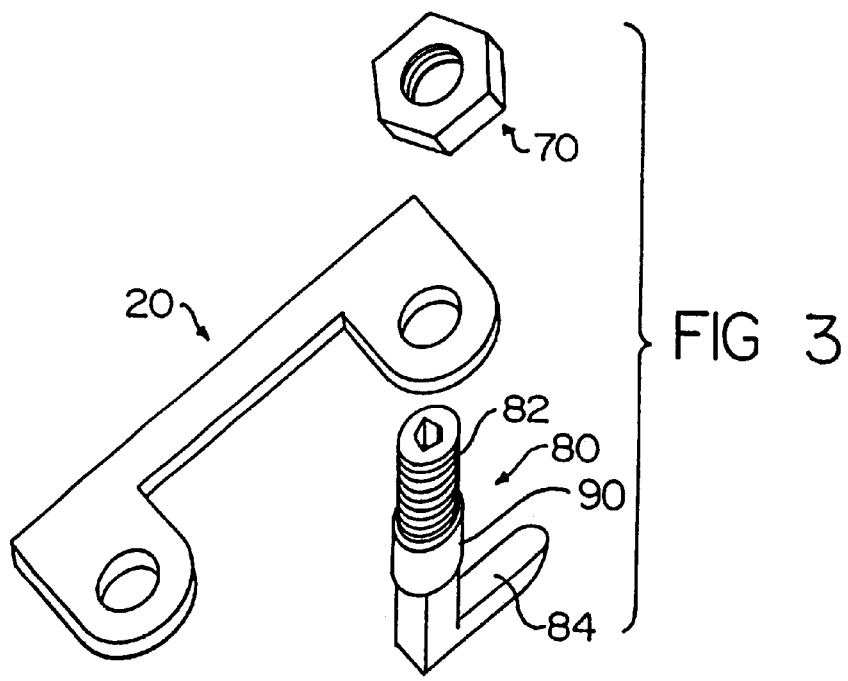
FIG. 3 is an exploded view of a pedicle or laminar hook, the link shown in FIG. 1B, and a locking nut according to another embodiment of the present invention.

With reference to FIG. 3, a laminar hook 80 is shown which can be used in addition to or in place of the bone bolts 50 of FIG. 2. While member 80 is referred to as a laminar hook, those skilled in the art will appreciate that pedicle hooks could be utilized as well. Laminar hook 80 incudes a hook or pad portion 84 which engages portions of the lamina of a respective vertebra. It will be appreciated that the hook portion 84 can be in a form other than the L-shape shown in FIG. 3 and, for example, can take the shapes shown in the aforementioned patents incorporated by reference in this application.

Hook member 80 further includes a threaded upper bolt portion 82 which is passed through the aforementioned aperture in one end of a link member, which link in FIG. 3 is in the form of the C-shaped plate member 20 (of FIG. 1B). Locking bolt 70 is then threaded onto portion 82 of hook member 80 to securely lock the link 20 to the vertebra.

FIG. 3 also shows a sleeve member 90 which is disposed over threaded portion 82 of hook 80 to adjust the height of the link member 20 with respect to the hook or pad portion 84. The proper height sleeve needed for a particular application will typically depend on the laminar thickness of a vertebra and will be determined intraoperatively by the surgeon. The sleeve 90 preferably will be provided in different sizes so that the surgeon can choose the proper size sleeve for the specific application.

With attention now directed to FIG. 7, a side elevational view of an exemplary rigid construct assembled from a plurality of link members in accordance with the present invention is indicated generally by reference numeral 400. The construct includes a plurality of links 410 connected end-to-end in chain-like fashion as described above. The construct 400 includes laminar or pedicle hooks 480 but it will be understood that the above-described bone bolts or screws can be used in addition to or in place of the hooks 480.

As shown in FIG. 7, sleeves 490 of various heights are interposed between the hook or pad portion 484 of each the hooks 480 and link members 410. In addition, a spacer member 500 is disposed between the two adjacent link members 410 on the right end of the construct to compensate for the difference in height thereof so as to permit the links to be connected substantially in parallel. The aforementioned means for enhancing the locking relationship, e.g., roughening or radial cuts, between the bolts or hooks and the links, the locking nuts 470 and bolts, between adjacent links, etc., can also be used.

It will be readily recognized that the construct shown in FIG. 7 is but one example of an application of the present invention. In addition, it will be appreciated that FIG. 7 shows a construct that can be connected to a similar construct by any of the aforementioned cross-tie mechanisms to provide a quadrilateral construct.

Another aspect of the present invention is shown in FIGS. 8A and 8B and includes link members which are pre-curved in the sagittal or lateral plane for treating various spinal conditions. The link 610 is plate-shaped and is similar to link 10 except that link 610 is pre-curved in the sagittal plane. As can be seen, concave and convex surfaces 620 and 622 are defined on opposite sides of link 610. FIGS. 8A and 8B show that the plane in which the link is pre-curved is substantially perpendicular to the plane in which the link is offset, i.e., the plane in which central portion 616 is offset from the ends 612, 614.

While link 610 is plate shaped, the present invention also includes rod-shaped links (as described is above and shown in FIG. 1C) which are pre-curved in a similar fashion. The end portions 612, 614 of link 610 are preferably flat so that apertures 618 properly engage the vertebrae attachment members. However, the entire link (and not just central portion 616) can be curved instead.

For example, the link 610 can be placed as shown in FIGS. 8A and 8B to treat lordosis (forward curvature of the lumbar or thoracic spine), while the link could be placed in reverse to treat kyphosis (backward convex curvature of the spine). It will be appreciated that pre-curving the links in a manner other than that shown in FIGS. 8A and 8B is possible to achieve links having shapes and/or curvatures suited for additional applications.

The pre-curved links made according to the present invention provide the surgeon with numerous curved spinal links from which can be selected the appropriate link member for a particular application. This is superior to the flat prior art links. The curvature of the present links is set during manufacturing by any suitable process, e.g. a forming or machining process, and thus the link curvature is precise and results in efficient application of force to the selected vertebrae.

Figure 9A:
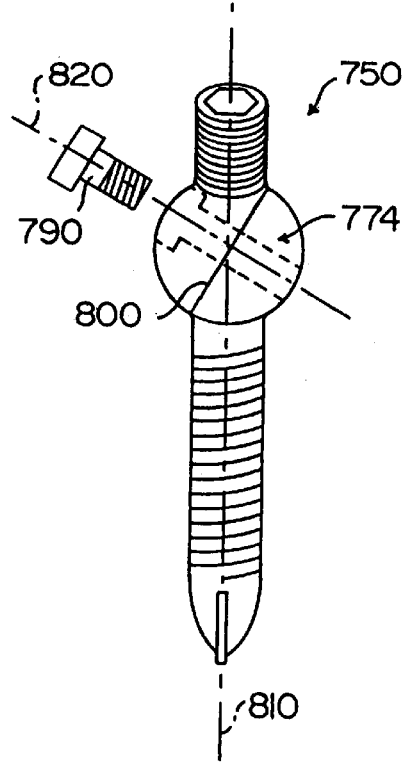
FIG. 9A is a perspective view of a multi-directional attachment device constructed according to the present invention.
Figure 9B:
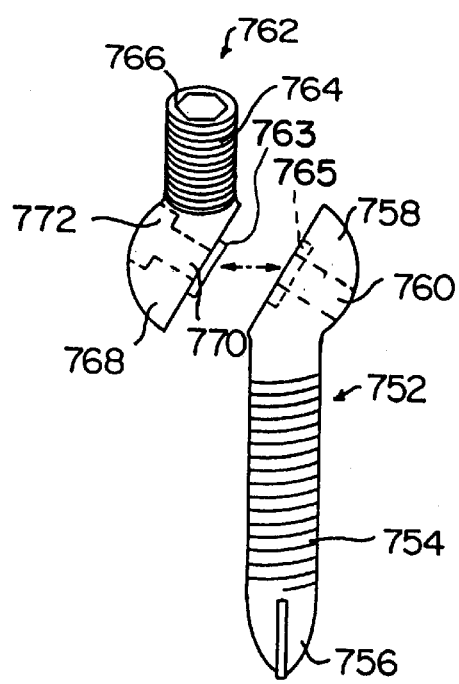
FIG. 9B is a perspective exploded view of the multi-directional attachment device depicted in FIG. 9A showing a modification thereto.
Figure 9C:
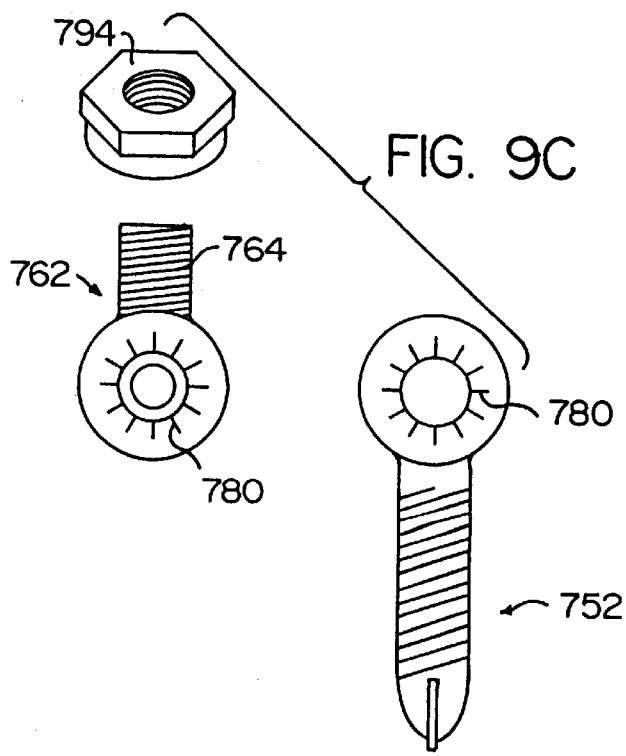
FIG. 9C is a perspective exploded view of the multi-directional attachment device depicted in FIG. 9A.

Referring now to FIGS. 9A–9C, a multi-directional attachment device constructed according to yet another aspect of the present invention is indicated generally by the reference numeral 750. The multi-directional attachment device 750 may be used with the above-described spinal treatment apparatus, e.g. in place of or in addition to bone bolt 50 shown in FIG. 2, or with various other spinal treatment apparatus or, still further, device 750 may be used with fixation apparatus for treating other bones than those in the spine. For example, the element 750 may be used with external fixation apparatus for treating long bones and the pelvis.

Multi-directional attachment device 750 includes two portions, namely, screw portion 752 and bolt portion 754. Screw portion 752 has an elongated section extending between opposite ends 756, 758, which elongated section has helical threads 754 (or another suitable cutting surface) formed thereon for engaging a bore formed in a vertebra or other bone (not shown). The screw portion 752 preferably has a hemispherically-shaped end 758 with a bore 760 extending therethrough. The end 758 of screw portion 752 has a flat face (FIG. 9C) with serrations or other interdigitating structure 30 780 formed thereon for reasons described below. The bore 760 preferably is centrally located with respect to hemispherically-shaped end 758 as seen in FIGS. 9B and 9C.

Bolt portion 762 includes opposite end portions 766 and 768. A threaded portion 764 extends from end 766 and includes threads (or other means) for engaging a locking nut after an apertured (or slotted) plate, rod, etc. has been positioned thereover as will be described below. Bolt portion 762 also include a bore 770 extending through hemispherically-shaped end 768, which bore aligns with bore 760 of screw portion 752 to receive means for fastening portions 752 and 762 together. The bore 770, however, includes a stepped portion 772 so that the enlarged head of a fastening means may be received in countersunk fashion so as to be substantially flush with the rounded portion of hemispherically-shaped end 768 of bolt portion 762. The end 768 of bolt portion 762 has serrations or other interdigitating structure 780 for locking same to the similarly configured face of end 758 of screw portion 752. The mating interdigitating surfaces may be in the form of serrations, ramped teeth, roughened surfaces or any other structure for rotationally locking the bolt portion 762 to the screw portion 752.

An example of means for fastening the screw and bolt portions together is shown in FIG. 9A and includes a lag-type set screw 790 that is threaded so as to mate with the threaded bores 760, 770 of the respective screw and bolt portions. The screw and bolt portions may be rotated with respect to each other and locked in position via set screw 790.

Referring to FIG. 9A, the hemispherically-shaped end portions 758, 768 of the respective screw and bolt portions 752, 762 are joined in face-to-face contact along the plane or equator 800 to form a substantially spherically-shaped central member 774 (with set screw 790 not in place). In a preferred embodiment of the multi-directional screw/bolt according to the present invention, the screw and bolt portions are coaxial, i.e. positioned so that the longitudinal axis of each extends alongline 810, the pivot axis 820 about which the respective portions are rotatable forms an oblique angle with the aforementioned longitudinal axis 810. That is, when the screw and bolt portions are positioned so as to be coaxial, the longitudinal axis thereof does not form a right angle with the pivot axis about which the portions may rotate.

Another preferred embodiment of the invention is shown in FIG. 9B and includes a projection 763 on the face of bolt portion 762 and a mating recess 765 on the face of screw portion 752 (or vice-versa). The projection 763 and recess 765 serve to facilitate proper engagement of the components as well as provide the attachment member with added shear strength.

This aspect of the invention permits the bolt portion 762 to extend from the center of the sphere 774 formed by the joined screw and bolt hemispherically-shaped ends, 758, 768. In other words, regardless of the angular position of bolt portion 762 relative to the screw portion 752, the threaded portion 764 of the bolt will always extend along a central axis of the aforementioned sphere. This feature permits the bolt 762 to engage the center of the opening in a plate, sod, etc. For example, it is known in the art to form a plate member with an opening for receiving a threaded attachment member secured to a vertebra. If the attachment member has a cylindrical or semi-cylindrical surface, the plate is formed with a concave depression adjacent the opening which depression seats on the cylindrical surface. Since the bolt portion 762 of the invention extends outwardly from the sphere along a central axis thereof, the plate (or other element) opening can be received on the bolt with the latter centrally located therein, and with the concave depression properly seated on sphere 774. Locking nut 794 then is threaded over bolt extension 764 to securely fix the plate to the multi-directional attachment device 750. This provides an extremely stable and secure assembly.

Figure 9D:
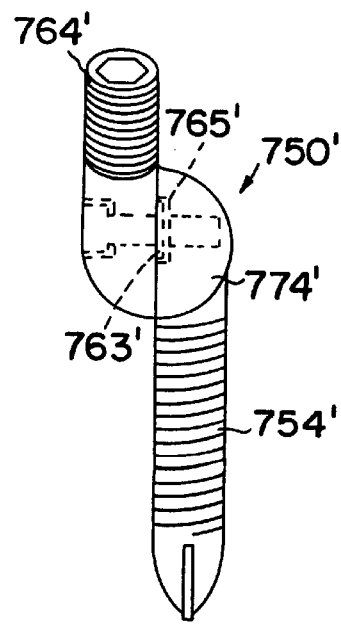
FIG. 9D is a perspective view of a multi-directional attachment device according to another embodiment of the present invention.

However, as seen in FIG. 9D, it also is possible to form a multi-directional attachment device 750' such that the bolt extension 764' does not extend from the center of the spherical portion 774' formed by the mating hemispherically-shaped end portions 768', 758'. The elongated screw section 754' also may not extend is from the center of end spherical portion 774'. The embodiment shown in FIG. 9B, however, illustrates the preferred construction of the multi-directional attachment device of the present invention.

The benefits obtained by the ability to independently position the bolt portion 762 with respect to the screw portion 752 will be apparent to those skilled in the art. It is possible to position the screw portion in an optimal location in the vertebrae (or other bone) without concern as to the angle that the screw forms with the desired position of a plate, rod, etc., because the bolt portion can be adjusted relative to the screw portion so as to engage the plate in a perpendicular manner.

Figure 10A:
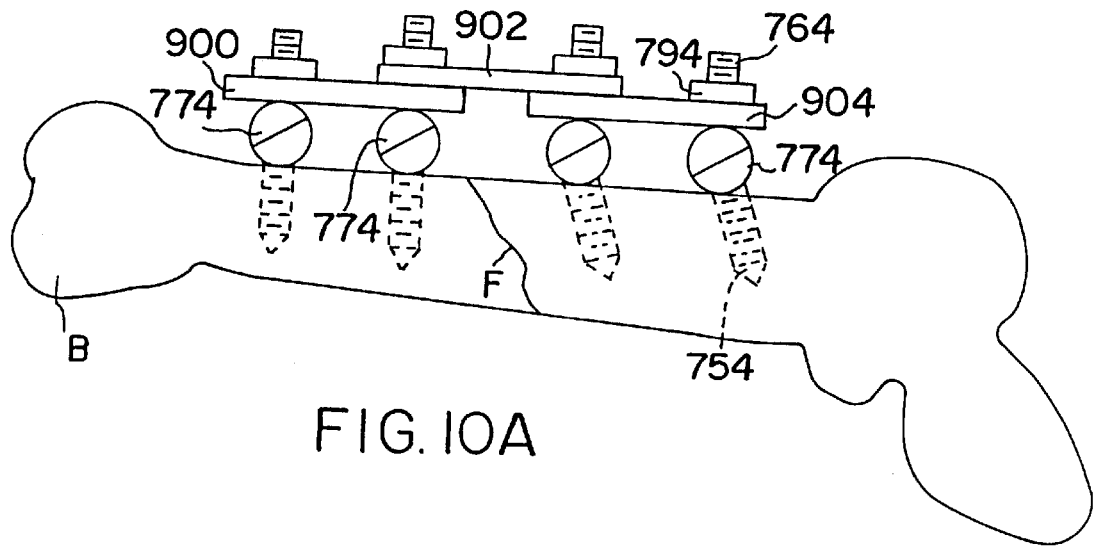
FIG. 10A is a front elevational view of the link member and multi-directional attachment device of the present invention used as an external bone fixation apparatus.

In another aspect of the present invention, a bone fixation system is provided for external applications, such as stabilizing bones which have been fractured, e.g., long bones, pelvic bones, etc. FIG. 10A depicts an external bone fixation system secured to a long bone B having a fracture F therein. The system includes a plurality of plates 900, 902, 904 which may have a structure according to the form of the spinal implant plates discussed above with respect to the aforementioned embodiments. A plurality of multi-directional attachment members having spherical portions 774 are provided, these members preferably having a structure described above in connection with FIGS. 9A–9C.

As can be seen in FIG. 10A, plate members 900 and 904 are secured to each portion of bone B on opposite sides of fracture F via respective pairs of multi-directional attachment members. These two plate members are joined to each other by a third plate member 902 the two ends of which respectively overlie an end of each plate 900, 904. The threaded section 754 of the screw portion 752 of each attachment member is positioned in an optimal location in bone B, and the extension 764 of the bolt portion 762 of each respective attachment member is angularly adjusted to engage the plate members in a desired fashion, e.g., perpendicularly. Locking nuts 794 are positioned on bolt portions 762 to lock the plates to the attachment members. This arrangement, which is a one-plane fixation of bone B, stabilizes the bone portions to permit healing of fracture F.

Figure 10B:
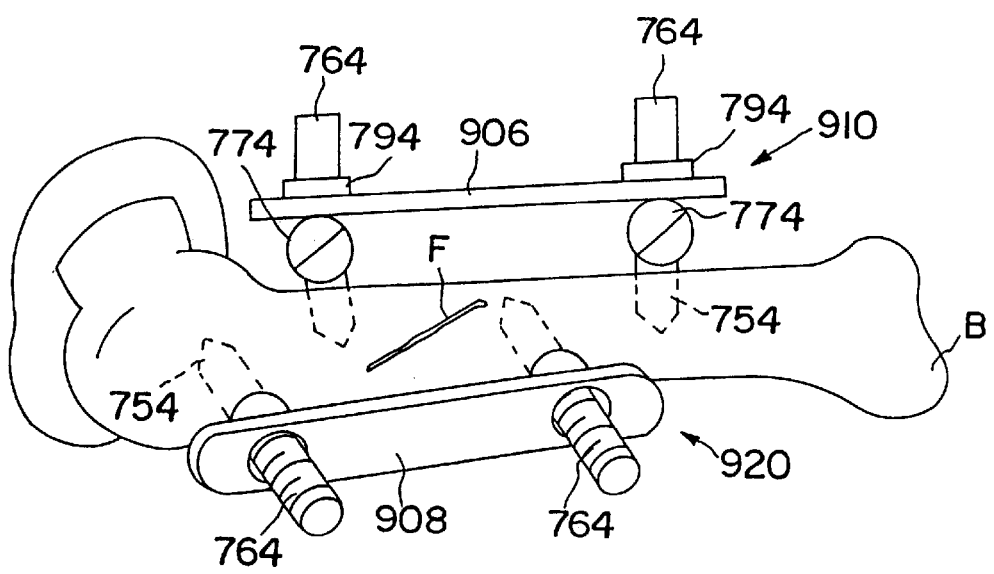
FIG. 10B is a side elevational view of the link member and multi-directional attachment device of the present invention used as an external bone fixation apparatus in a two plane fixation system.

FIG. 10B depicts a two-plane fixation of a bone B with a fracture F. Specifically, a first fixation assembly 910 includes a plate member 906 secured to bone B in a first plane via a pair of multi-directional attachment members with spherical portions 774 formed by mating end portions of bolt and screw portions, and locking nuts 794 as described above. A second fixation assembly 920 includes a plate member 908 secured to bone B in a different plane via a second pair of attachment members (the locking washers not being attached to bolt extensions 764 on which plate 908 is mounted in FIG. 10B). The embodiment in FIG. 10B stabilizes the fractured bone B in two planes and is suitable, e.g., for use in applications requiring considerable stabilization forces.

FIG. 11 shows a further application of an external bone fixation system wherein the system is secured to a pelvic bone PB. The system includes a first fixation assembly 930 including a plate member 900 secured to a side of the pelvis via a pair of multi-directional attachment members having spherical portions 774. As seen in FIG. 11, the screw sections 754 are positioned at a desired location in the bone while the bolt extensions 764 are adjusted relative sections 754 to engage plate 900 in a perpendicular manner. A second fixation assembly 940 is secured to the opposite side of the pelvis via a second pair of attachment members. The respective fixation assemblies 930, 940 may be connected to each other by cross-link members (not shown) constructed according to the above-embodiments (e.g., as in FIGS. 4 and 6). Such connection of the in plate assemblies may be carried out along the anterior (line A in phantom) or posterior (line P in phantom) surface of the pelvis.

Those skilled in the art will appreciate that the embodiments of FIGS. 10A, 10B and 11 illustrate only exemplary non-spinal applications of the bone-fixation systems according to the present invention. Other applications and uses, of course, will be apparent to persons skilled in the art.

It is apparent that the present invention provides a link member that can be secured to other link members in chain-like fashion so as to permit connection of a series of points forming a nonlinear path on several vertebrae. In this manner, force can be selectively exerted on a particular vertebra or vertebrae to move the vertebra to a desired position and to maintain same in that position.

The present invention also includes links which overcome the problem with prior art plate systems in which minimal bone volume is available for grafts or fusion by providing an offset link structure. According to one aspect of the present invention, the central portion of the link is laterally displaced relative to the end portions thereof so as to leave the surface of the lateral margin of a vertebra to which the link is attached substantially uncovered.

The present invention further provides a multi-directional attachment device which includes a screw portion and a bolt portion. The device permits the screw portion to be secured in bone at a desired angular position, and the bolt portion attached thereto to be angularly adjusted so as to engage a spinal implant plate, rod, or an external bone fixation device in a desired manner. For example, by adjusting the bolt portion relative to the screw portion, the bolt portion can engage the fixation device in a perpendicular manner to enhance the overall stability and effectiveness of the system, as well as substantially prevent trauma to bone tissue.

Although the invention has been described with reference to particular embodiments, it is to be understood that the embodiments are merely illustrative of the application of the principles of the invention. Numerous configurations may be made therewith and other arrangements may be devised without departing from the spirit and scope of the invention.

What is claimed is:

1. An integrally formed one-piece spinal implant link member adapted for linking two adjacent vertebrae in a fixed relationship, said link member having opposite ends and a central portion connecting said opposite ends, said opposite ends each having an aperture therein configured to receive means for attaching said link member to said two adjacent vertebrae, whereby said aperture in one of said opposite ends is adapted to be attached to one of said adjacent vertebrae and said aperture in the other of said opposite ends is adapted to be attached to the other of said adjacent vertebrae, said central portion being offset from said opposite ends of said link member and defining an open space between said opposite ends, said open space being disposed adjacent said central portion and extending away from said central portion to a line connecting said apertures in said opposite ends, and each of said opposite ends having means to lock said opposite end to an opposite end of a second link member in an overlapping manner precluding relative rotation of said link member and said second link member, whereby said means for attaching said link member to one of said adjacent vertebrae also secures said link member and said second link member together in a fixed angular position relative to each other and to said one of said adjacent vertebrae.

2. The link member of claim 1, wherein said central portion is V-shaped.

3. The link member of claim 2, wherein said link member is a flat plate.

4. The link member of claim 1, wherein said central portion is C-shaped.

5. The link member of claim 4, wherein said link member is a flat plate.

6. The link member of claim 1, wherein said link member is a flat plate.

7. The link member of claim 6, wherein said central portion is offset relative to said opposite ends so as to leave the surface of the lateral margin of both of said adjacent vertebrae substantially uncovered when said link member is attached to said adjacent vertebrae.

* * * * *